(12) United States Patent
Buge et al.

(10) Patent No.: US 10,987,307 B2
(45) Date of Patent: *Apr. 27, 2021

(54) NO-RINSE CHEMICAL FOAM COMPRISING IVERMECTIN

(71) Applicant: GALDERMA RESEARCH & DEVELOPMENT, Biot (FR)

(72) Inventors: Jean-Christophe Buge, Nice (FR); Karine Nadau-Fourcade, Villeneuve Loubet (FR)

(73) Assignee: Galderma Research & Development, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/764,804

(22) PCT Filed: Sep. 27, 2016

(86) PCT No.: PCT/EP2016/073013
§ 371 (c)(1),
(2) Date: Mar. 29, 2018

(87) PCT Pub. No.: WO2017/055296
PCT Pub. Date: Apr. 6, 2017

(65) Prior Publication Data
US 2019/0192433 A1    Jun. 27, 2019

(30) Foreign Application Priority Data

Sep. 29, 2015    (FR) ...................................... 1559206

(51) Int. Cl.
*A61K 9/12* (2006.01)
*A61K 9/00* (2006.01)
(Continued)

(52) U.S. Cl.
CPC ............. *A61K 9/122* (2013.01); *A61K 9/007* (2013.01); *A61K 9/0014* (2013.01);
(Continued)

(58) Field of Classification Search
CPC ...... A61K 9/0014; A61K 9/007; A61K 9/122; A61K 31/7048; A61K 47/12; A61P 17/06; A61P 17/04
See application file for complete search history.

(56) References Cited

U.S. PATENT DOCUMENTS 5,952,372 A    9/1999    McDaniel
6,133,310 A    10/2000    Parks
(Continued)

FOREIGN PATENT DOCUMENTS

CN         104382863 A       3/2015
DE    10 2008 029 357 A1    12/2009
(Continued)

OTHER PUBLICATIONS

International Search Report and English translation dated Dec. 1, 2016 corresponding to International Patent Application No. PCT/EP2016/073013, 7 pages.
(Continued)

*Primary Examiner* — Jianfeng Song
(74) *Attorney, Agent, or Firm* — Foley & Lardner LLP; Sunk Talapatra

(57) ABSTRACT

A self-foaming composition is described that includes ivermectin, for a no-rinse topical application and for application to the skin. The composition can include: at least one intermediate composition B including a gas-generating agent; at least one intermediate composition A including an agent for activating the gas-generating agent; and ivermectin being present in the composition A, in the composition B, or simultaneously in the two compositions A and B. Also described, is a kit or a single container including a plurality of compartments including such a composition.

28 Claims, 4 Drawing Sheets

(51) Int. Cl.
*A61K 31/7048* (2006.01)
*A61K 47/12* (2006.01)
*A61K 47/02* (2006.01)
*A61P 17/04* (2006.01)
*A61P 17/10* (2006.01)
*A61P 17/06* (2006.01)

(52) U.S. Cl.
CPC .......... *A61K 31/7048* (2013.01); *A61K 47/02* (2013.01); *A61K 47/12* (2013.01); *A61P 17/04* (2018.01); *A61P 17/06* (2018.01); *A61P 17/10* (2018.01)

(56) References Cited

U.S. PATENT DOCUMENTS

| | | | |
|---|---|---|---|
| 6,177,092 B1 * | 1/2001 | Lentini | A61K 8/046 424/401 |
| 6,649,186 B1 * | 11/2003 | Robinson | A61K 9/0007 424/466 |
| 10,449,175 B2 | 10/2019 | Buge et al. | |
| 2002/0061855 A1 | 5/2002 | Parks | |
| 2004/0151671 A1 | 8/2004 | Abram et al. | |
| 2004/0184992 A1 | 9/2004 | Abram | |
| 2005/0123487 A1 | 6/2005 | Spadini et al. | |
| 2006/0189695 A1 * | 8/2006 | Uchida | A61K 9/145 514/573 |
| 2007/0237724 A1 | 10/2007 | Abram et al. | |
| 2009/0093550 A1 | 4/2009 | Rolfes et al. | |
| 2009/0191248 A1 | 7/2009 | Hoffman et al. | |
| 2009/0214628 A1 | 8/2009 | De Rijk et al. | |
| 2010/0221350 A1 * | 9/2010 | Baudonnet | A61K 31/59 424/490 |
| 2010/0291160 A1 | 11/2010 | Carver et al. | |
| 2011/0008267 A1 | 1/2011 | Arkin et al. | |
| 2011/0236503 A1 | 9/2011 | Kalli | |
| 2011/0311592 A1 * | 12/2011 | Birbara | A61K 8/498 424/400 |
| 2012/0114574 A1 * | 5/2012 | Touitou | A61K 9/0014 424/61 |
| 2012/0282188 A1 * | 11/2012 | Feltin | A61Q 19/00 424/44 |
| 2013/0244976 A1 * | 9/2013 | Inamoto | A61K 8/046 514/57 |
| 2013/0317108 A1 | 11/2013 | At | |
| 2013/0338230 A1 * | 12/2013 | At | A61K 47/36 514/569 |
| 2013/0338235 A1 | 12/2013 | At | |
| 2014/0364504 A1 | 12/2014 | Uddin | |
| 2015/0306124 A1 | 10/2015 | Manetta et al. | |
| 2017/0172877 A1 | 6/2017 | Buge et al. | |
| 2017/0172972 A1 | 6/2017 | Buge et al. | |
| 2018/0064638 A1 | 3/2018 | Tamarkin et al. | |

FOREIGN PATENT DOCUMENTS

| | | |
|---|---|---|
| EP | 1 043 023 A1 | 10/2000 |
| FR | 2761600 A1 | 10/1998 |
| FR | 2924944 A1 | 6/2009 |
| FR | 2943914 A1 | 10/2010 |
| JP | 2002-529391 A | 9/2002 |
| JP | 2004-217675 A | 8/2004 |
| WO | WO-00/27356 A1 | 5/2000 |
| WO | WO-03/030664 A1 | 4/2003 |
| WO | WO-2004/037225 A2 | 5/2004 |
| WO | WO-2005/058272 A1 | 6/2005 |
| WO | WO-2009/069006 A2 | 6/2009 |
| WO | WO-2012/001065 A2 | 1/2012 |
| WO | WO-2012/085480 A1 | 6/2012 |
| WO | WO-2012/085481 A1 | 6/2012 |
| WO | WO-2012/085483 A1 | 6/2012 |
| WO | WO-2014/201541 A1 | 12/2014 |
| WO | WO-2015/082659 A1 | 6/2015 |

OTHER PUBLICATIONS

Written Opinion of the International Searching Authority dated Dec. 1, 2016 corresponding to International Patent Application No. PCT/EP2016/073013, 6 pages.

Onset Therapeutics, LLC, "Benzefoam Ultra", Drug Information Online—Drugs.com, Apr. 3, 2011, XP002739766. 9 pages.

Wikimedia Commons; "Citric Acid Speciation" https://commons.wikimedia.org/wiki/File:Citric_acid_speciation.png; accessed Jan. 10, 2020 (Year: 2011).

* cited by examiner

NO-RINSE CHEMICAL FOAM COMPRISING IVERMECTIN

CROSS-REFERENCE TO PRIOR APPLICATIONS

This application is a National Stage of PCT/EP2016/073013, filed Sep. 27, 2016, and designating the United States (published on Apr. 6, 2017, as WO 2017/055296 A1), which claims priority under 35 U.S.C. § 119 to French Application No. 1559206, filed Sep. 29, 2015, each hereby expressly incorporated by reference in its entirety and each assigned to the assignee hereof.

The present invention relates to a pharmaceutical or cosmetic composition for topical application in the form of a leave-on foam comprising a compound of the avermectin family, preferably ivermectin.

The present invention also relates to a topical pharmaceutical composition in the form of a leave-on foam comprising a compound of the avermectin family, preferably ivermectin, for its use in patients with inflammatory skin pathologies.

The avermectin class is a group of macrocyclic lactones produced by the *Streptomyces avermitilis* bacterium (J. E. F. Reynolds (Ed.) (1993) Martindale. The extra pharmacopoeia. 29th Edition. Pharmaceutical Press, London). Among these macrocyclic lactones belonging to the avermectin class, mention may be made of ivermectin, avermectin, abamectin, doramectin, eprinomectin, selamectin, aversectin B, AB or C, emamectin B1b and derivatives thereof, or latidectin.

According to the invention, the compound of the avermectin family is preferentially ivermectin.

Ivermectin is a mixture of 22,23-dihydroavermectin B1a and 22,23-dihydroavermectin B1b. Ivermectin predominantly contains 22,23-dihydroavermectin B1a.

Ivermectin is known in the prior art for its antiparasitic and antihelmintic properties. In the middle of the 1980s, the molecule was presented as a broad-spectrum antiparasitic medicament for veterinary use (W. C. Campbell et al., (1983). Ivermectin: a patent new antiparasitic agent. Science, 221, 823-828.). It is efficacious against the majority of common intestinal worms (except for tapeworms), the majority of acarids, and some lice. It has high affinity for glutamate-dependent chloride channels, especially those which are dependent on the neuromediator GABA (gamma-aminobutyric acid), present in invertebrate nerve and muscle cells, giving it antiparasitic activity. More particularly, its binding to these channels promotes an increase in membrane permeability to chloride ions leading to hyperpolarization of the nerve or muscle cell. This results in neuromuscular paralysis which can lead to the death of certain parasites. Ivermectin also interacts with other chlorine channels.

Ivermectin is conventionally used in the dermatological treatment of endoparasitic conditions such as onchocerciasis and myiasis.

U.S. Pat. Nos. 6,133,310 and 5,952,372 also describe the use of ivermectin in the treatment of rosacea in order to reduce and eliminate the parasite *Demodex folliculorum*. Ivermectin is also known for its use in the treatment and/or prevention of a large number of inflammatory skin pathologies such as acne, eczema, atopic dermatitis or psoriasis and in particular rosacea.

The mechanism of action of ivermectin in rosacea inflammatory lesions is based on its anti-inflammatory and anti-parasitic properties. Ivermectin eliminates the *Demodex* acarids which are involved in the inflammatory skin eruptions. Since these acarids may be present both on the skin and on the scalp, cleansing compositions containing ivermectin which are suitable either for cleansing the scalp or for cleansing the skin, or even both simultaneously, are of particular interest in this pathology and the treatment thereof.

Dermatological conditions are often associated with increased skin sensitivity, particularly in the case of rosacea which is an inflammatory dermatosis mainly affecting the central part of the face and which is characterized, inter alia, by redness of the face, hot flushes and facial erythema. Patients suffering from rosacea have very sensitive skin, and cleansing products must have very high tolerance. Now, the majority of cleansing products have a high content of cleansing and foaming surfactants so as to generate a substantial amount of foam to aid cleansing. However, foaming surfactants are generally irritant. In addition, some compounds used in compositions intended for a known topical application may result in side-effects that may limit the use and thus the effectiveness thereof. For example, some active principles have the major drawback of inducing irritation which may result in mediocre tolerance of the product. This may thus create, on the part of the patient, behavior of non-compliance with the treatment and dissatisfaction regarding said treatment.

There is thus a need for novel galenical forms and in particular compositions of foam or foaming type in which ivermectin is stable, effective and pleasant to apply, and which ensure good tolerance of the product.

The Applicant has, surprisingly, developed foaming pharmaceutical compositions comprising a compound of the avermectin family, especially ivermectin, which are very well tolerated on sensitive skin. Foams make it possible to overcome problems of tolerance by better control of the dose, by virtue of their spreading properties and their low density.

The composition according to the present invention may be used advantageously in the case of patients with inflammatory skin pathologies such as rosacea, but also acne, eczema or atopic dermatitis.

The composition according to the invention has the advantage of being an emulsion in the form of a foam which is generated at the time of use and which is very well tolerated.

After its application, the composition according to the invention is not removed by rinsing.

One of the advantages of the composition of the invention is that it is particularly well tolerated, despite the fact that it is not removed by rinsing, as is shown by the examples illustrating one of the methods of evaluating the tolerance which are presented below, and in the light of the figures attached to the present patent application.

Figure 1:
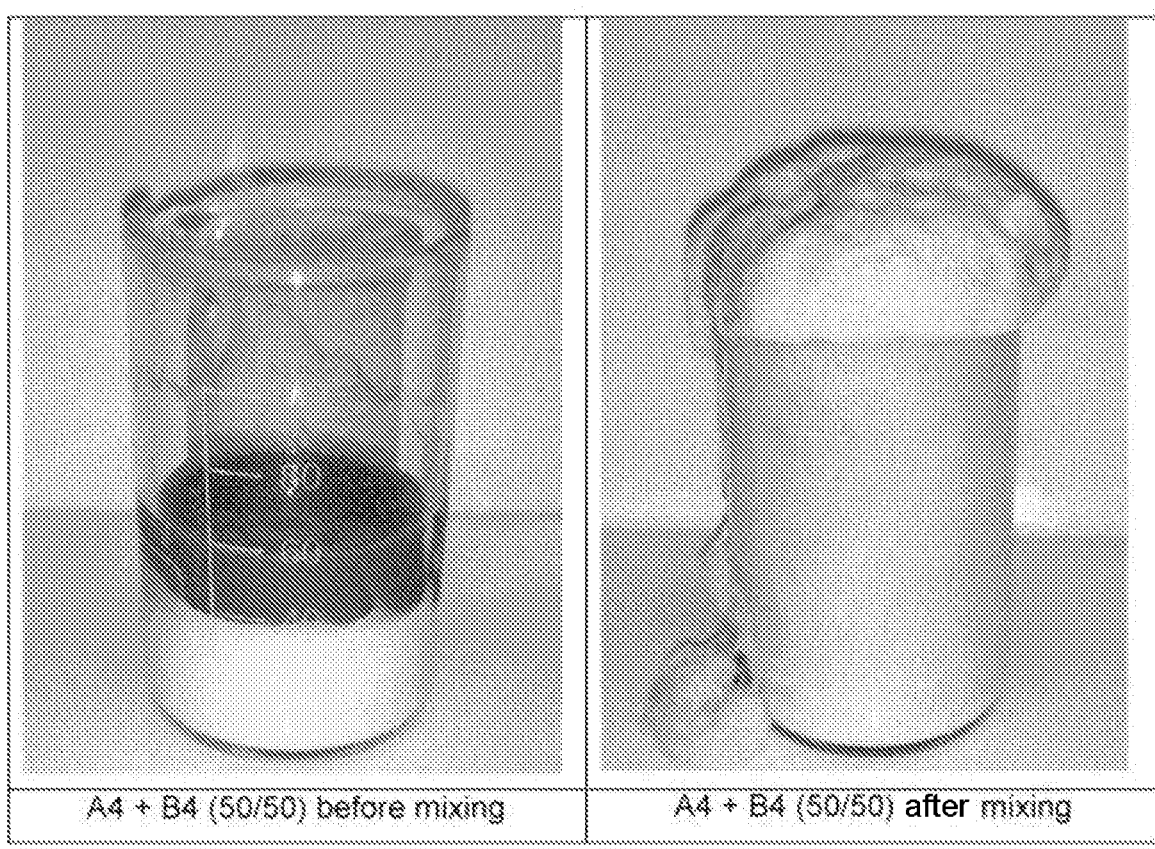
FIG. 1 shows photographs of a first composition in accordance with the invention obtained by mixing the two intermediate compositions A4 and B4 described in the examples, immediately after mixing them and then when the reaction between these two compositions is complete (maximum foam volume).

Various methods exist for evaluating the tolerance of a pharmaceutical or cosmetic product for cutaneous use, among which may be mentioned the in vivo "in used" test or "human patch test" but also the in vitro test, such as the test for measurement of the irritation on Reconstructed Human Epidermis (RHE) described in the OECD TG 439 protocol. The latter method is described in detail in example 3.

Foams or foaming compositions currently exist on the market. However, they all have a certain number of drawbacks:

This is because three types of foams or foaming compositions exist:

Aerosols, in which the foam is generated by a propellant gas but with the drawback of being aerosols having the well-known risks of the latter (contamination and breathing risks in particular).

Expanded creams, in which air bubbles are introduced into the product via a particular manufacturing process. This process has the drawback of being restricting at the industrial level and requires major capital expenditure with regard to the packaging equipment.

Foaming formulations which are low in foaming surfactants but packaged a packaging equipped with a mechanical foam-generating system (pump with grille of Pulvorex type). This type of formulation requires the use of foaming surfactants, which may lead to irritation in the case of leave-on products.

Thus, the need therefore remains to develop a pharmaceutical composition, the galenical form of which is different from the known galenical forms, in order, inter alia, to provide compositions intended for topical application containing ivermectin that is stable in well-tolerated compositions intended for topical application to human beings, in particular leave-on compositions (i.e. the composition is not removed by rinsing after it has been applied).

The aim of the present invention is thus to provide a composition which meets these needs.

The Applicant has thus developed a novel pharmaceutical composition intended for a leave-on topical application, which is in the form of a foam which advantageously does not contain any foaming surfactant. The term "foaming surfactant" defines surfactants which produce a voluminous, stable and creamy foam when they are mixed with water according to tests that are well known to those skilled in the art.

The following constitute foaming surfactants: anionic surfactants, cationic surfactants, amphoteric surfactants and nonionic surfactants of the family of alkylpolyglucosides and glucamides.

The galenical form according to the invention has the advantage of ensuring good stability of ivermectin. Furthermore, this formulation advantageously results in the production of a mild foam which is fully tolerated and non-irritant, which allows better coverage of the area to be treated and which makes it possible to overcome the problems of tolerance by better control of the dose, by virtue of the spreading properties and the low density of the foam. Furthermore, the release-penetration study described in example 5 confirms the need to obtain a foam that remains at the surface of the skin, so as to act efficiently against *Demodex* which resides on the skin.

Finally, advantageously, this galenical form does not require, for the implementation thereof, the use of propellant gases or aerosols. Thus, "aerosol" or "spray" foams are excluded from the scope of the invention. Likewise, the foams of the prior art of expanded cream and/or foaming formulation type requiring a mechanical foam-generating system (Pulvorex type) are also excluded from the invention.

Finally, a subject of the present invention is the cosmetic use of the composition according to the invention, by topical application of this composition to the skin, and also a medicament intended for topical application to the skin, comprising such a composition.

A subject of the present invention is also the composition according to the invention, for its use in the treatment and/or prevention of inflammatory skin pathologies. Preferably, the composition according to the invention is used for treating and/or preventing acne, eczema, atopic dermatitis, psoriasis or rosacea and more preferentially for treating and/or preventing rosacea.

The present invention will be described in greater detail in the description and the examples hereinbelow.

The composition according to the invention is capable of taking the form of a foam solely by virtue of its composition, and may also be defined as a self-foaming composition for topical application.

A first subject of the present invention is consequently a composition containing ivermectin, intended for leave-on topical application, which is provided in the form of a foam, advantageously of semisolid consistency, which advantageously does not contain any foaming surfactant and which comprises a medium that is pharmaceutically compatible with leave-on topical application, in particular to the skin and integuments.

The term "composition in the form of a foam" (also referred to hereinbelow as a self-foaming composition) means a composition of semisolid consistency having an aerated form comparable to a foam as presented in FIGS. 1 and 2.

The self-foaming composition according to the present invention comprises two intermediate compositions or formulations in variable proportions and in particular the ingredients below:
  at least one intermediate composition or formulation A comprising an agent for activating the gas-generating agent described below;
  at least one intermediate composition or formulation B comprising a gas-generating agent;
  ivermectin contained in at least one of said intermediate formulations A and B.

According to the invention, the composition is self-foaming, i.e. it foams by simple mixing of the intermediate compositions A and B. A subject of the invention is also the composition in foam form resulting from the mixing of said intermediate compositions A and B.

According to the invention, each intermediate composition (or formulation) may have a viscosity (measured at 25° C. and at atmospheric pressure) of between 1 cP and 500 000 cP, advantageously between 500 cP and 350 000 cP, measured with a conventional method of Brookfield RV Dy-II type: spindle 6, speed 2.

According to the invention, the gas generated by the gas-generating agent may be any physiologically compatible gas which allows the production of a foam, for instance carbon dioxide ($CO_2$) or oxygen ($O_2$). Preferably, the gas generated from the gas-generating agent is carbon dioxide ($CO_2$).

According to the invention, since the gas concentration may vary, the amount of bubbles in the composition may vary and may thus give a composition which may range from not very aerated to very strongly aerated.

According to the invention, the term "agent for activating the gas-generating agent" means an ingredient which, by chemical reaction with the gas-generating agent, releases a gas. Preferentially, an acid/base reaction is involved.

Thus, according to the invention, the self-foaming composition may preferentially be in any form ranging from aerated to a highly expanded foam.

The composition according to the invention is suitable for topical application and may also comprise a physiologically acceptable medium, i.e. a medium that is compatible with the skin and integuments. It is preferably a pharmaceutically acceptable medium.

In addition, the composition may comprise any active agent that may have activity, optionally therapeutic activity. These active agents may be chosen, inter alia, from emollients, humectants, free-radical scavengers, anti-inflammatory agents, vitamins, depigmenting agents, antiacne agents, antiseborrheic agents, antifungal agents, keratolytic agents, sunscreens, slimming agents and skin-coloring agents.

According to the invention, the composition in foam form (i.e. ready to be applied) may have a pH of between 2 and 8, preferentially between 4 and 7.

Insofar as the intermediate composition(s) (or formulation(s)) require storage in at least two compartments for reasons of stability of the ingredients, the present invention relates either to a single compartmentalized container (each compartment receiving one intermediate formulation) and preferably comprising two or three compartments, or to a kit comprising each intermediate formulation stored independently from each other and physically separated.

Intimate extemporaneous mixing (directly on the skin or on any other support) of the intermediate formulations makes it possible to obtain the composition in foam form according to the invention.

More specifically, the intermediate composition (or formulation) A may be in the form of a solution, an emulsion (lotion, cream, emulsifier-free cream, milk or fluid cream) or a gel. This composition advantageously contains the agent for activating the gas-generating agent, preferentially an acid, in a sufficient amount (which may be in the form of an acid/base buffer at acidic pH), which may be, as a nonlimiting example, the citric acid/sodium citrate combination.

Formulation B may be in the form of a solution, a gel or an emulsion (lotion, cream, emulsifier-free cream, milk or fluid cream). This composition advantageously contains, in a sufficient amount, a gas-generating agent which may in particular be sodium bicarbonate.

Thus, a subject of the invention is also a kit or a single multi-compartment container as defined previously, for the extemporaneous preparation of a composition in foam form according to the invention, separately comprising at least two intermediate formulations (or intermediate compositions):
- an intermediate composition A comprising at least one agent for activating the gas-generating agent; and
- an intermediate composition B comprising at least one gas-generating agent;
- ivermectin being contained in composition A or in composition B or simultaneously in the two compositions A and B.

Gas-Activating Agent:

The agent for activating the gas-generating agent (also referred to as the "gas-activating agent") is a compound which reacts with the gas-generating agent via a chemical reaction (preferably an acid/base reaction) which releases a gas.

It is advantageously an acid, a partially salified polyacid salt or a buffer solution of a weak acid and of its conjugate base, or a mixture of such compounds.

According to the invention, the acid/base buffer of said acid may be any acid/base buffer of the weak acid, for instance a citric acid/sodium citrate buffer or a tartaric acid/sodium tartrate buffer. Mention will preferably be made of α-hydroxy acids, which are weak acids preferentially with a pKa of between 2 and 6, such as citric acid, tartaric acid, malic acid or lactic acid, but also phosphoric acid and pyrophosphoric acid and optionally the partially salified salts thereof, such as disodium pyrophosphate or sodium dihydrogen phosphate, also known as monosodium phosphate.

Preferentially, according to the invention, the gas-activating agent is chosen from a tartaric acid/tartrate salt (for example sodium tartrate) buffer; a citric acid/sodium citrate buffer alone; phosphoric acid, monosodium phosphate, disodium pyrophosphate, which are alone or as a mixture with a citric acid/sodium citrate buffer.

According to a very preferred embodiment, the gas-activating agent is a citric acid/sodium citrate buffer, alone or as a mixture with monosodium phosphate and/or disodium pyrophosphate.

In compositions for sensitive skin or for damaged skin, such as acneic skin, the content of citric acid/sodium citrate is preferably less than or equal to 2.4%, relative to the total weight of the intermediate composition A, so as to limit any risk of stinging. In order to improve the tolerance and to avoid the sensation of stinging, preferably, the citric acid/sodium citrate buffer is used as a mixture with disodium pyrophosphate or sodium dihydrogen phosphate.

According to the invention, said gas-activating agent may be present in the intermediate formulation A in an amount that may range from 0.001% to 95% by weight relative to the total weight of the intermediate composition A.

Gas-Generating Agent:

The term "gas-generating agent" means any agent which has the property of generating a gas via a chemical reaction. Mention will be made in this regard of any compound which, when it is mixed with a weak acid, can form a gas via a chemical reaction equivalent to the following:

$$NaHCO_3 + RCOOH \rightarrow RCOONa + H_2O + CO_2$$

According to the invention, the gas generated from the gas-generating agent present in the intermediate composition B is preferably carbon dioxide ($CO_2$).

According to the invention, the gas-generating agent is preferably chosen from sodium bicarbonate, potassium bicarbonate, sodium carbonate and potassium carbonate, and mixtures thereof.

Preferentially, according to the invention, the intermediate formulation B comprises an agent which generates carbon dioxide, this agent particularly preferably being sodium bicarbonate.

Said gas-generating agent may be present in the intermediate formulation B in an amount ranging from 1% to 10% by weight and preferentially from 2% to 8% by weight, relative to the weight of the intermediate composition B.

According to the invention, the intermediate formulation A may have an acidic pH, advantageously of between 1.0 and 6.0, and the intermediate formulation B may have a basic pH, advantageously of between 7 and 12.

According to the invention, one or both of the intermediate formulations comprise ivermectin in an amount of between 0.01% and 6% by weight relative to the total weight of the total composition.

Preferably, the total composition (mixture of the intermediate formulation A with the intermediate formulation B) contains ivermectin in concentrations ranging from 0.5% to 5% by weight and more preferentially from 0.8% to 4% by weight, relative to the weight of the total formulation.

In the present description, the term "total composition" or "total formulation" means the composition of the product in foam form after said intermediate compositions have been mixed. Ivermectin is contained in intermediate composition A or in intermediate composition B or simultaneously in the two compositions.

The intermediate formulation A may be in any galenical form that is compatible with the galenical form desired for the final composition obtained by mixing formulation A with formulation A. Advantageously, formulation A may be a gel, a solution, a suspension or an emulsion (cream, surfactant-free cream, lotion, milk or fluid cream).

The intermediate formulation B may be in any galenical form that is compatible with the galenical form desired for the final composition obtained by mixing formulation B with formulation B. Advantageously, formulation B may be a gel, a solution, a suspension or an emulsion (cream, surfactant-free cream, lotion, milk or fluid cream).

According to one embodiment of the invention, one of the two intermediate formulations (i.e. intermediate formulation A or intermediate formulation B) is in the form of a gel. In this embodiment, the other intermediate formulation is preferably not in gel form.

Each intermediate formulation of the kit or of the multi-compartment container as defined previously in accordance with the invention comprises a physiologically acceptable medium which conveys the compound(s) and which is chosen such that the compounds are capable of reacting with each other to form a self-foaming composition during the mixing of at least the intermediate formulations A and B.

Thus, the extemporaneous mixing of at least two formulations, for example formulation A and formulation B, creates the composition in foam form according to the invention.

During the mixing of the two formulations A and B, the gas-generating agent, such as sodium bicarbonate, reacts with the gas-activating agent, such as the acid, and thus gives in particular the salt corresponding to the acid, water and $CO_2$ gas. It is this gas, trapped in the bubbles of the composition, which creates the foam which characterizes the self-foaming composition of the invention.

Thus, by mixing at least intermediate formulation A and intermediate formulation B, the foam composition, referred to as the total composition, according to the invention is obtained.

Unreacted gas-activating agent and/or gas-generating agent may, of course, remain in the composition obtained after mixing at least formulations A and B.

Advantageously, the kit or the single multi-compartment container according to the invention may be designed so that, during the preparation of the composition according to the invention, the intermediate formulations A and B can be mixed in an A/B weight ratio ranging from 0.5 to 2, preferentially from 0.5 to 1.5, more preferentially close to 1 (i.e. from 0.9 to 1.1) and even more preferentially 1. This means that the kit can be designed to simultaneously release doses (by weight) of the intermediate compositions A and B that may be in a weight ratio ranging from 2 doses of B per 1 dose of A to 2 doses of A per 1 dose of B, preferably from 2 doses of B per 1 dose of A to 3 doses of A per 2 doses of B. According to a preferred embodiment of the invention, the kit is designed to simultaneously release 1 dose by weight of A and 1 dose by weight of B.

According to the invention, the kit may be in any form that is compatible with, on the one hand, separate storage of the intermediate formulations A and B and, on the other hand, the ability to perform extemporaneous mixing of A and B.

For example, the intermediate formulations A and B may be packaged in a case with at least two separate compartments, each containing A or B.

According to another aspect, the kit may be in the form of a syringe having at least two separate bodies, each equipped with a piston, said two bodies containing the respective formulations A and B and being designed to simultaneously release, by exerting a force on the piston, the desired doses of formulations A and B.

The invention also relates to a process for preparing a composition in foam form according to the invention, characterized in that, in order to obtain the self-foaming composition, an intermediate formulation A and an intermediate formulation B of the kit as are defined above are mixed extemporaneously in relative weight proportions A/B that may range from 0.5 to 2, preferentially from 0.5 to 1.5 and more preferentially 1.

In order to obtain an optimum foam (final composition), the inventors experimentally sought the optimum contents of gas-generating agent (preferably sodium bicarbonate) and of gas-activating agent (preferably citric acid and/or disodium pyrophosphate and/or sodium dihydrogen phosphate or monosodium phosphate).

Thus, it was determined experimentally that when the gas-activating agent is citric acid, the citric acid/sodium bicarbonate weight ratio is advantageously between 0.1 and 2, preferentially between 0.5 and 1 and very preferably equal to 0.7.

Similarly, it was determined experimentally that when the gas-activating agent is disodium pyrophosphate, the disodium pyrophosphate/sodium bicarbonate weight ratio is between 0.5 and 5, preferentially between 1 and 3 and very preferably equal to 2.4.

Similarly, it was determined experimentally that when the gas-activating agent is sodium dihydrogen phosphate, the sodium dihydrogen phosphate monohydrate/sodium bicarbonate weight ratio is between 0.5 and 5, preferentially between 1 and 3 and very preferably equal to 2.

The sodium bicarbonate/citric acid, sodium bicarbonate/sodium pyrophosphate and sodium bicarbonate/sodium hydrogen phosphate ratios are illustrated in example 4.

Surprisingly, the citric acid/sodium citrate, disodium pyrophosphate or sodium dihydrogen phosphate combination and a gelling system that is compatible with the galenical form made it possible to obtain a formulation with very stable physicochemical properties.

Example 2B below shows that the compositions according to the present invention have both excellent physical and chemical stability.

A composition is regarded as being physically stable when its organoleptic characteristics, its pH, its viscosity and the homogeneity of ivermectin do not change over time under various temperature conditions: room temperature (RT), 30° C. and 40° C.

According to the invention, room temperature corresponds to a temperature ranging from 15° C. to 25° C.

A composition is regarded as being chemically stable when the content of active principle it contains does not change over time under various temperature conditions (room temperature (RT) and 40° C.).

According to the invention, the composition is regarded as being stable when the content of ivermectin (expressed by weight relative to the weight of the intermediate formulation) and measured via any standard method and especially HPLC, is included in the specifications ranging from 90% to 110%.

The composition according to the invention may also comprise one or more agents chosen from dispersants, solubilizers, stabilizers, preserving agents, fatty substances, thickeners, dyes, fragrances, surfactants, gelling agents, complexing agents, neutralizers, non-foaming emulsifying agents, fillers, sequestrants, reducing agents, odor maskers, plasticizers, softeners, moisturizers, pigments, clays, mineral fillers, mineral colloids, polymers, proteins, nacreous agents, waxes, oils, for instance paraffins or silicones, fatty acids, solid esters of fatty alcohols or of fatty acids, gums and wetting agents.

Water-soluble dyes, such as FD&C Blue 1 (of empirical formula $C_{37}H_{34}N_2Na_2O_9S_3$), and liposoluble dyes such as Sudan Red III or Nile Red, have the advantage of coloring one of the formulation intermediates. This coloring makes it possible to monitor the satisfactory mixing of the two formulation intermediates and to highlight the formation of the foam.

Gelling Agents for the Intermediate Formulation Comprising the Gas Activator

The intermediate composition A advantageously containing at least one gas-activating agent preferably contains at least one gelling agent and/or suspending agent.

Since formulation A may contain large amounts of acid and of electrolytes, it may prove to be difficult to stabilize. The viscosity and the suspending power of these formulations are often difficult to ensure over time.

As nonlimiting examples of gelling agents and/or suspending agents which are resistant simultaneously to electrolytes and to acidic pH values and which may be included in the compositions A according to the invention, mention may be made of ready-to-use mixtures, such as the ammonium acrylate/acrylamide copolymer & polyisobutene & polysorbate 20 mixture sold by SEPPIC under the name Sepiplus 265®, the acrylamide/sodium acryloyldimethyl taurate copolymer & isohexadecane & polysorbate 80 mixture sold by SEPPIC under the name Simulgel 600 PHA®, the polyacrylate-13 & polyisobutene & polysorbate 20 mixture sold by SEPPIC under the name Sepiplus 400®, the acrylates/C10-30 alkyl acrylate crosspolymer sold by the company Lubrizol under the names Pemulen™ TR-1 Polymeric Emulsifier and Pemulen™ TR-2 Polymeric Emulsifier, polysaccharides with, as nonlimiting examples, xanthan gum, such as Xantural 180® sold by the company Kelco, gellan gum sold under the name Kelcogel® by the company Kelco, *sclerotium* gum sold under the name Amigel® by Alban Muller Industrie, guar gum and derivatives thereof, such as the hydroxypropyl guar sold under the name Jaguar HP-105® by Rhodia, cellulose and derivatives thereof, such as microcrystalline cellulose and sodium carboxymethyl cellulose sold under the name Blanose CMC 7H4XF® by the company Hercules, hydroxypropylmethylcellulose, in particular the product sold under the name Methocel E4M® Premium by the company Dow Chemical, or hydroxyethylcellulose, in particular the product sold under the name Natrosol HHX 250® by the company Aqualon, the family of the magnesium aluminum silicates, such as Veegum K®, Veegum Plus® or Veegum Ultra® sold by the company Vanderbilt, bentonite sold uner the name Polargel HV®, the family of modified starches, such as the modified potato starch sold under the name Structure Solanace®, the family of carrageenans, in particular divided into four main families: κ, λ, β and ω, such as the Viscarin® and Gelcarin® products sold by the company IMCD. Alternatively, polyvinyl alcohol, also known under the abbreviation PVA, sold by Merck under the name Polyvinyl Alcohol 40-88®. Preferably, Veegum K®, Simulgel 600 PHA® and Xantural 180® will be used alone or in combination in pairs or all three together.

The gelling agent as described above may be used at preferential concentrations ranging from 0.001% to 15% and more preferentially ranging from 0.15% to 5% by weight relative to the weight of the intermediate formulation A.

Gelling Agents for the Intermediate Formulation Containing the Gas Generator

As nonlimiting examples of gelling agents and/or suspending agents and/or gelling agents that are simultaneously resistant to electrolytes and two basic pH values and which may be included in the intermediate compositions B according to the invention, mention may be made of acrylic acid polymers such as the acrylates/C10-30 alkyl acrylate crosspolymer such as the "electrolyte-insensitive" carbomers sold under the name Ultrez 20®, Ultrez 10@, Carbopol 1382® or Carbopol ETD2020NF®, Aqua SF1® sold by the company Lubrizol, the ammonium acrylate/acrylamide copolymer & polyisobutene & polysorbate 20 mixture sold by SEPPIC under the name Sepiplus 265®, the acrylamide/sodium acryloyldimethyl taurate copolymer & isohexadecane & polysorbate 80 mixture sold by SEPPIC under the name Simulgel 600 PHA®, the polyacrylates-13 & polyisobutene & polysorbate 20 mixture sold by SEPPIC under the name Sepiplus 400®, the acrylates/C10-30 alkyl acrylate crosspolymer sold by the company Lubrizol under the names Pemulen™ TR-1 Polymeric Emulsifier and Pemulen™ TR-2 Polymeric Emulsifier, polysaccharides with, as nonlimiting examples, xanthan gum, such as Xantural 180® sold by the company Kelco, gellan gum sold under the name Kelcogel® by the company Kelco, *sclerotium* gum sold under the name Amigel® by Alban Muller Industrie, guar gum and derivatives thereof, such as the hydroxypropyl guar sold under the name Jaguar HP-105® by Rhodia, cellulose and derivatives thereof, such as microcrystalline cellulose and sodium carboxymethyl cellulose sold under the name Blanose CMC 7H4XF® by the company Hercules, hydroxypropylmethylcellulose, in particular the product sold under the name Methocel E4M® Premium by the company Dow Chemical, or hydroxyethylcellulose, in particular the product sold under the name Natrosol HHX 250® by the company Aqualon, bentonite sold under the name Polargel HV®, the family of the magnesium aluminum silicates, such as Veegum K®, Veegum Plus® or Veegum Ultra® sold by the company Vanderbilt, the family of modified starches, such as the modified potato starch sold under the name Structure Solanace® or the tapioca meal known under the name Naviance Tapioca P® sold by AkzoNobel, or the family of carrageenans, in particular divided into four main families: κ, λ, β and ω, such as the Viscarin® and Gelcarin® products sold by the company IMCD. Preferably, Veegum K®, Simulgel 600 PHA® and Xantural 180® will be used alone or in combination in pairs or all three together.

The gelling agent as described above may be used at preferential concentrations ranging from 0.001% to 15% and more preferentially ranging from 0.15% to 5% by weight relative to the weight of the intermediate formulation B.

Humectants

Among the humectants and/or emollients which may act as skin moisturizer and facilitate the application of the formulation, use is optionally made, without this list being limiting, of compounds such as a polyol that is water-miscible at room temperature (25° C.) chosen especially from polyols especially containing from 2 to 20 carbon atoms, preferably containing from 2 to 10 carbon atoms and preferentially containing from 2 to 6 carbon atoms, such as glycerol, glycol derivatives such as propylene glycol, butylene glycol, pentylene glycol, hexylene glycol, dipropylene glycol, diethylene glycol or 1,3-propylene glycol sold under the name Zemea by the company DuPont Tate & Lyle Bio Products Company, LLC and mixtures thereof, but also sugars (for example glucose or lactose), polyethylene glycols (PEG) (for example Lutrol E400®), urea, and amino acids (for example serine, citrulline, arginine, asparagine or alanine).

As preferred humectant and/or emollient, mention may be made of glycerol and propylene glycol.

The humectants may be used, alone or in combination, at preferential concentrations ranging from 0.001% to 30% and more preferentially ranging from 0.01% to 10% by weight relative to the weight of the total formulation.

Chelating Agents

Among the chelating agents, mention may be made, as nonlimiting examples, of ethylenediaminetetraacetic acid (EDTA), diethylenetriaminepentaacetic acid (DTPA), ethylenediaminebis(O-hydroxyphenylacetic acid) (EDDHA), hydroxy-2-ethylenediaminetriacetic acid (HEDTA), ethyldiaminebis(O-hydroxy-p-methylphenyl)acetic acid (EDDHMA) and ethylenediaminebis(5-carboxy-2-hydroxyphenyl)acetic acid (EDDCHA).

As preferred chelating agent, mention may be made of ethylenediaminetetraacetic acid (EDTA) sold especially under the name Titriplex II®; it may be used at preferential concentrations ranging from 0.001% to 1% and more preferentially from 0.05% to 0.1% by weight relative to the weight of the total formulation.

Excipients or Active Agents with Complementary Properties

The composition according to the invention may contain one or more excipients with specific properties, for instance, as nonlimiting examples, allantoin with anti-irritant properties, dipotassium glycyrrhizate for its anti-inflammatory properties, or alternatively the cicatrizing agent α-bisabolol or lithium digluconate for its anti-redness properties.

In a particular embodiment, the composition according to the invention may also contain one or more other pharmaceutical active principles, for instance brimonidine or a nonsteroidal anti-inflammatory agent such as diclofenac or adapalene.

Fillers and Particles

Fillers and/or particles may be used to stabilize and boost the foam. Some of them have the specific property of being positioned at the water/air interface and of thus stabilizing this interface. Fillers that may be mentioned include talc, metal oxides such as zinc oxide, titanium dioxide TiO2 T2000 sold by the company Merck under the name Eusolex® T-2000, clays such as laponites, bentones or bentonites, but also cellulose ethers such as Methocel® K100 LV sold by the company Dow, silicas such as Aerosil® R972 sold by the company Evonik or Silice HDK® H13L sold by Wacker; they may be used at concentrations ranging from 0.01% to 10% by weight relative to the weight of the total formulation.

Oils of the Fatty Phase

The composition according to the invention may also comprise a fatty phase. This fatty phase may be present in one and/or the other of the intermediate compositions A and B. Depending on the galenical form of the intermediate formulations, the fatty phase may represent from 0% to 95% by weight relative to the weight of each intermediate formulation.

The fatty phase of the composition according to the invention may comprise, for example, plant, mineral, animal or synthetic oils, silicone oils, and mixtures thereof.

As examples of mineral oils, mention may, for example, be made of liquid paraffins of various viscosities, such as Primol 352®, Marcol 82® and Marcol 152® sold by the company Esso.

As plant oils, mention may be made of sweet almond oil, palm oil, soybean oil, sesame oil, sunflower oil and olive oil.

As animal oils or the substitute thereof of plant origin, mention may be made of lanolin, squalene, fish oil with, as a derivative, the perhydrosqualene sold under the name Sophiderm® by the company Sophim.

As synthetic oils, mention may be made of an ester such as cetearyl isononanoate, for instance the product sold under the name Cetiol SN PH® by the company Cognis France, isononyl isononanoate such as Dub ININ® sold by the company Stéarineries Dubois, isopropyl myristate sold under the name Crodamol IPM by the company Croda, diisopropyl adipate, for instance the product sold under the name Crodamol DA® by the company Croda, isopropyl palmitate, for instance the product sold under the name Crodamol IPP® by the company Croda, and caprylic/capric triglyceride, such as Miglyol 812® sold by the company Univar. As hydrogenated polyisobutenes, mention may be made of the Parleam® products sold by the company Rossow, the C12-15 alkyl benzoate sold under the name Crodamol AB by the company Croda, octyldodecanol or Eutanol G sold by the company BASF, oleyl alcohol sold under the name Kollicream OA by the company BASF, PPG-11 Stearyl Ether or Arlamol P511E sold by the company Croda.

As silicone oils, mention may be made of a dimethicone, for instance the product sold under the name Q7-9120 Silicone Fluid® with a viscosity from 20 cSt to 12 500 cSt, by the company Dow Corning, or a cyclomethicone, for instance the product sold under the name ST-Cyclomethicone 5NF®, also by the company Dow Corning.

A preferred oil that may be mentioned is caprylic/capric triglyceride, PPG-11 stearyl ether or isopropyl palmitate.

These oils may be present, alone or in combination, in contents ranging from 0.5% to 50% by weight and preferentially from 2% to 30% by weight relative to the weight of the total composition.

Nonliquid Fatty Substances

The composition according to the invention, and in particular the intermediate formulation B, may also comprise solid fatty substances such as natural or synthetic waxes, fatty acids such as stearic acid, fatty alcohols such as Speziol C18® Pharma or Speziol C16® sold by the company Cognis, and texturing agents of tribehenate type, such as Compritol 888® sold by the company Gattefosse or hydrogenated castor oils such as Cutina HR® sold by the company Cognis or glyceryl stearate such as Geleol® sold by the company Gattefosse or DC 9045 Elastomer Blend® sold by the company Dow Corning.

These nonliquid fatty substances may be used alone or as a mixture from 0% to 30% by weight relative to the weight of the total formulation. However, exceptional foam quality has been observed when fatty alcohols of formula $CH_3(CH_2)_nOH$ (n is between 11 and 23) are present in contents of greater than 1% by weight relative to the weight of the total formulation.

Nonionic Emulsifiers

The composition according to the invention, and especially the intermediate formulation B, may also comprise one or more nonionic emulsifiers.

Preferred emulsifiers that may be mentioned include hydrophilic emulsifiers such as glyceryl stearate (and) PEG-100 stearate sold under the name Arlacel 165FL® by the company Uniqema, lipophilic emulsifiers such as Glucate SS® and Glucamate SSE®, polyoxyethylene (21) stearyl ether sold under the name Brij 721® by the company Uniqema or also in the same family Brij S2® and Brij S20®. The self-emulsifying wax sold by Croda under the name of Polawax NF®. Mention may also made of nonionic surfactants with a high HLB, sorbitan esters such as POE(20) sorbitan monooleate sold under the name Tween 80® (HLB=15), POE(20) sorbitan monostearate sold under the name Tween 60® (HLB=14.9), fatty alcohol ethers such as POE (21) stearyl ether (HLB=15.5), or ceteareth-20 sold under the name of Eumulgin B2 PH® by Cognis (HLB of 15.5), or nonionic surfactants with a low HLB, sorbitan esters, such as sorbitan monostearate (sold under the name of Span 60® by Uniqema), glycerol esters such as glyceryl monostearate (Cutina GMS® from Cognis), sucrose esters with a low HLB, such as sucrose distearate. In another form according to the invention, the surfactants that may be used are polyglycerol esters. They are esters of polyglycerolated fatty acids obtained by condensation of glycerol. Glycolipid emulsifiers, such as Montanov 202® sold by the company SEPPIC. Some emulsifiers may be sold in the form of a mixture, such as Emulium Kappa® and Emulium Delta® sold by Gattefossé. These surfactants may be used, alone or as a mixture, so that the HLB of the system is greater than 11 and preferentially greater than 15.

Such emulsifiers may be used at between 0.01% and 30% by weight, relative to the weight of the total composition, preferentially between 0.1% and 15% and more preferentially between 0.5% and 7%.

In a preferred embodiment, the emulsifier is Ceteareth-20 alone or as a mixture, and especially with sorbitan monostearate.

Preserving Agents

Examples of preserving agents that may be mentioned include benzalkonium chloride, bronopol, chlorhexidine, chlorocresol and derivatives thereof, ethyl alcohol, phenoxyethanol, potassium sorbate, diazolidinyl urea, benzyl alcohol, parabens and sodium benzoate, or mixtures thereof.

As preferred preserving system, mention may be made of phenoxyethanol alone or as a mixture with any other preserving agent and in particular with those mentioned previously.

The examples that follow illustrate the invention without limiting its scope.

EXAMPLES

Example 1: Formulation Examples

Formulation Examples A: Intermediate Compositions a Containing the Gas-Activating Agent Formulations A1, A7 and A10 were prepared according to the following protocol:

Step 1: At a temperature above 60° C., add the main gelling agent (Veegum K) with stirring to the main water phase.

Step 2: Add the acidic buffer agents and then cool to 40° C.

Step 3: Add the other gelling agent(s) with stirring.

Step 4: Add the other excipients of the formulation with stirring.

Formulation A2 was prepared according to the following protocol:

Step 1: At a temperature of 75° C., disperse the gelling agent and dissolve the water-soluble excipients.

Step 2: In parallel, heat the fatty phase (surfactants, waxes and oils)+the propylene glycol/oleyl alcohol/ivermectin mixture to 75° C.

Step 3: At 75° C., prepare the emulsion.

Step 4: Add the additives such as the preserving agents at a temperature suitable for the additive.

Step 5: Neutralize the mixture.

Step 6: Add the acidic buffer agents.

Formulations A3, A4, A5, A6, A8 and A9 are prepared according to the protocol of formula A2.

In the formulation examples below, the amounts are expressed relative to the weight of the intermediate formulation rather than relative to the weight of the total formulation.

Example A1

| INCI Name | % |
| --- | --- |
| WATER | QS 100 |
| DISODIUM EDTA | 0.1 |
| MAGNESIUM ALUMINIUM SILICATE | 2.5 |
| XANTHAN GUM | 1.5 |
| CITRIC ACID | 1.4 |
| SODIUM CITRATE | 1 |
| DISODIUM PYROPHOSPHATE | 7.2 |
| POLOXAMER 124 | 0.2 |
| PROPYLENE GLYCOL | 4 |
| SODIUM BENZOATE | 0.2 |

Example A2

| INCI Name | % |
| --- | --- |
| WATER | QS 100 |
| XANTHAN GUM | 0.5 |
| MAGNESIUM ALUMINIUM SILICATE | 2.5 |
| CETOSTEARYL ALCOHOL | 3 |
| CETEARETH-20 | 3 |
| GLYCERYL DIBEHENATE | 3 |
| CAPRYLIC/CAPRIC TRIGLYCERIDE | 6 |
| CITRIC ACID | 1.5 |
| SODIUM CITRATE | 0.5 |
| SODIUM DIHYDRONEPHOSPHATE | 6.2 |
| OLEYL ALCOHOL | 2 |
| PROPYLENE GLYCOL | 2 |
| PHENOXYETHANOL | 0.8 |
| IVERMECTIN | |
| WATER | QS 100 |

-continued

| INCI Name | % |
|---|---|
| XANTHAN GUM | 0.5 |
| ACRYLAMIDE, AMPS COPOLYMER DISPERSION 40%/ISOHEXADECANE/POLYSORBATE 80 | 1.5 |
| CETOSTEARYL ALCOHOL | 3 |
| CETEARETH-20 | 3 |
| GLYCERYL DIBEHENATE | 3 |
| CAPRYLIC/CAPRIC TRIGLYCERIDE | 6 |
| CITRIC ACID | 1.5 |
| SODIUM CITRATE | 0.5 |
| SODIUM DIHYDROGEN PHOSPHATE | 6.2 |
| OLEYL ALCOHOL | 2 |
| PROPYLENE GLYCOL | 2 |
| PHENOXYETHANOL | 0.8 |
| IVERMECTIN | 2 |

Example A3

Example A4

| INCI Name | % |
|---|---|
| WATER | QS 100 |
| DISODIUM EDTA | 0.1 |
| XANTHAN GUM | 0.5 |
| ACRYLAMIDE, AMPS COPOLYMER DISPERSION 40%/ISOHEXADECANE/POLYSORBATE 80 | 1.5 |
| CETOSTEARYL ALCOHOL | 3 |
| CETEARETH-20 | 3 |
| GLYCERYL DIBEHENATE | 3 |
| CYCLOPENTASILOXANE | 2 |
| PPG-11 STEARYL ETHER | 5 |
| CITRIC ACID | 1.5 |
| SODIUM CITRATE | 0.5 |
| SODIUM DIHYDROGEN PHOSPHATE | 6.2 |
| OLEYL ALCOHOL | 2 |
| PROPYLENE GLYCOL | 2 |
| PHENOXYETHANOL | 1 |
| IVERMECTIN | 2 |

Example A5

| INCI Name | % |
|---|---|
| WATER | QS 100 |
| XANTHAN GUM | 0.5 |
| MAGNESIUM ALUMINIUM SILICATE | 2.5 |
| CETOSTEARYL ALCOHOL | 3 |
| CETEARETH-20 | 3 |
| GLYCERYL DIBEHENATE | 3 |
| CAPRYLIC/CAPRIC TRIGLYCERIDE | 6 |
| CITRIC ACID | 1.5 |
| SODIUM CITRATE | 0.5 |
| SODIUM DIHYDROGEN PHOSPHATE | 6.2 |
| OLEYL ALCOHOL | 2 |
| PROPYLENE GLYCOL | 2 |
| PHENOXYETHANOL | 0.8 |

Example A6

| INCI Name | % |
|---|---|
| WATER | QS 100 |
| XANTHAN GUM | 0.5 |
| MAGNESIUM ALUMINIUM SILICATE | 1 |
| ISOPROPYL PALMITATE | 4 |
| IVERMECTIN | 2 |
| CETYL ALCOHOL | 3.5 |
| STEARYL ALCOHOL | 2.5 |
| SORBITAN MONOSTEARATE | 2 |
| PROPYL PARABEN | 0.1 |
| DIMETHICONE 20 CST | 0.5 |
| CETEARETH 20 | 3 |
| GLYCEROL | 4 |
| METHYL PARABEN | 0.2 |
| DISODIUM EDTA | 0.05 |
| CITRIC ACID | 1.5 |
| SODIUM CITRATE | 0.5 |
| SODIUM DIHYDROGEN PHOSPHATE | 6.2 |
| OLEYL ALCOHOL | 2 |
| PROPYLENE GLYCOL | 2 |
| PHENOXYETHANOL | 1 |

Example A7

| INCI Name | % |
|---|---|
| WATER | QS 100 |
| DISODIUM EDTA | 0.1 |
| XANTHAN GUM | 0.7 |
| MAGNESIUM ALUMINIUM SILICATE | 2.5 |
| SODIUM BENZOATE | 0.2 |
| DISODIUM PYROPHOSPHATE | 7.2 |
| CITRIC ACID | 1.4 |
| SODIUM CITRATE | 1 |
| POLOXAMER 124 | 0.2 |
| IVERMECTIN | 2 |
| PROPYLENE GLYCOL | 4.0 |

Example A8

| INCI Name | % |
|---|---|
| WATER | QS 100 |
| XANTHAN GUM | 0.5 |
| ACRYLAMIDE, AMPS COPOLYMER DISPERSION 40%/ISOHEXADECANE/POLYSORBATE 80 | 1.5 |
| ISOPROPYL PALMITATE | 4 |
| IVERMECTIN | 2 |

-continued

| INCI Name | % |
| --- | --- |
| CETYL ALCOHOL | 3.5 |
| STEARYL ALCOHOL | 2.5 |
| SORBITAN MONOSTEARATE | 2 |
| PROPYL PARABEN | 0.1 |
| DIMETHICONE 20 CST | 0.5 |
| CETEARETH 20 | 3 |
| GLYCEROL | 4 |
| METHYL PARABEN | 0.2 |
| DISODIUM EDTA | 0.05 |
| CITRIC ACID | 1.5 |
| SODIUM CITRATE | 0.5 |
| SODIUM DIHYDROGEN PHOSPHATE | 6.2 |
| OLEYL ALCOHOL | 2 |
| PROPYLENE GLYCOL | 2 |
| PHENOXYETHANOL | 1 |

Example A9

| INCI Name | % |
| --- | --- |
| WATER | QS 100 |
| XANTHAN GUM | 0.5 |
| ACRYLAMIDE, AMPS COPOLYMER DISPERSION 40%/ ISOHEXADECANE/ POLYSORBATE 80 | 1.5 |
| CAPRYLIC/CAPRIC TRIGLYCERIDE | 4.5 |
| IVERMECTIN | 2 |
| CETYL ALCOHOL | 3.5 |
| STEARYL ALCOHOL | 2.5 |
| SORBITAN MONOSTEARATE | 2 |
| PROPYL PARABEN | 0.1 |
| CETEARETH 20 | 3 |
| GLYCEROL | 4 |
| METHYL PARABEN | 0.2 |
| DISODIUM EDTA | 0.05 |
| CITRIC ACID | 1.5 |
| SODIUM CITRATE | 0.5 |
| SODIUM DIHYDROGEN PHOSPHATE | 6.2 |
| OLEYL ALCOHOL | 2 |
| PROPYLENE GLYCOL | 2 |
| PHENOXYETHANOL | 1 |

Example A10

| INCI Name | % |
| --- | --- |
| WATER | QS 100 |
| XANTHAN GUM | 0.5 |
| MAGNESIUM ALUMINIUM SILICATE | 2.5 |
| GLYCEROL | 6 |
| DISODIUM EDTA | 0.5 |
| CITRIC ACID | 1.5 |
| SODIUM CITRATE | 0.5 |
| SODIUM DIHYDROGEN PHOSPHATE | 6.2 |
| METHYL PARABEN | 0.2 |
| IVERMECTIN | 2 |

Formulation Examples B

Intermediate Compositions B Comprising the Gas-Generating Agent:

The intermediate formulations B are prepared according to the following process:

Step 1': At a temperature above 60° C., add the gelling agents with stirring to the main water phase.

Optional step 2': In parallel, heat the fatty phase (containing the oils, the waxes and the surfactants) to a temperature above 60° C. and incorporate the ivermectin.

Step 3' I: At a temperature above 60° C., prepare the emulsion by adding the fatty phase to the main phase.

Step 4': Add the additives such as the preserving agents or ethanol at a temperature suitable for the additive.

Step 5': Neutralize the mixture.

Step 6': At a temperature below 40° C., add the sodium bicarbonate.

Example B1

| INCI Name | % |
| --- | --- |
| WATER | QS 100 |
| MAGNESIUM ALUMINIUM SILICATE | 2.5 |
| XANTHAN GUM | 0.6 |
| POLYSORBATE 80 | 0.8 |
| STEARETH-20 | 2.8 |
| CETOSTEARYL ALCOHOL | 1.5 |
| MINERAL OIL | 8 |
| TRIETHANOLAMINE | 1.2 |
| SODIUM HYDROGEN CARBONATE | 5 |

Examples B2 and B3

| INCI NAME | B2 % | B3 % |
| --- | --- | --- |
| WATER | QS 100 | QS 100 |
| SODIUM CARBOXYMETHYLCELLULOSE | 0.5 | 0.2 |
| HYDROXYETHYLCELLULOSE | 1 | 0.1 |
| STEARETH-20 | 1.8 | 1.8 |
| GLYCERYL STEARATE (AND) PEG-100 STEARATE | 2.7 | 2.7 |
| CETOSTEARYL ALCOHOL | 1 | 7 |
| HYDROGENATED POLYISOBUTENE | 9 | 9 |
| TRIETHANOLAMINE | 1.2 | 1.2 |
| PROPYLENE GLYCOL | 5 | 5 |
| PHENOXYETHANOL | 1 | 1 |
| SODIUM HYDROGEN CARBONATE | 3 | 3 |

Example B4

| INCI Name | % |
| --- | --- |
| WATER | QS 100 |
| MAGNESIUM ALUMINUM SILICATE | 2.5 |
| XANTHAN GUM | 0.7 |
| DISODIUM EDTA | 0.1 |
| SODIUM HYDROXYDE | 0.019 |
| SODIUM HYDROGEN CARBONATE | 5 |
| PHENOXYETHANOL | 8 |
| BENZYL ALCOHOL | 0.2 |
| FD&C BLUE 1 | 0.005 |

Example B5

| INCI Name | % |
| --- | --- |
| WATER | QS 100 |
| MAGNESIUM ALUMINUM SILICATE | 3.5 |
| XANTHAN GUM | 1 |
| POLYSORBATE 80 | 2 |
| STEARIC ACID | 3 |
| CETOSTEARYL ALCOHOL | 1.5 |
| HYDROGENATED POLYISOBUTENE | 8 |
| TRIETHANOLAMINE | 1.8 |
| SODIUM HYDROGEN CARBONATE | 3 |
| PHENOXYETHANOL | 0.8 |

Example B6

| INCI Name | % |
| --- | --- |
| WATER | QS 100 |
| DISODIUM EDTA | 0.1 |
| XANTHAN GUM | 0.5 |
| ACRYLAMIDE, AMPS COPOLYMER DISPERSION 40%/ISOHEXADECANE/POLYSORBATE 80 | 1.5 |
| CETOSTEARYL ALCOHOL | 3 |
| CETEARETH-20 | 3 |
| GLYCERYL DIBEHENATE | 3 |
| CYCLOPENTASILOXANE | 2 |
| PPG-11 STEARYL ETHER | 5 |
| SODIUM HYDROGEN CARBONATE | 5 |
| OLEYL ALCOHOL | 2 |
| PROPYLENE GLYCOL | 2 |
| PHENOXYETHANOL | 1 |
| SODIUM HYDROXYDE | QS pH |
| IVERMECTIN | 2 |

Example B7

| INCI Name | % |
| --- | --- |
| WATER | QS 100 |
| MAGNESIUM ALUMINUM SILICATE | 2.5 |
| XANTHAN GUM | 0.5 |
| CETEARETH-20 | 3 |
| CETOSTEARYL ALCOHOL | 3 |
| GLYCERYL DIBEHENATE | 3 |
| CAPRYLIC/CAPRIC TRIGLYCERIDE | 6 |
| SODIUM HYDROXYDE | 0.09 |
| PHENOXYETHANOL | 0.8 |
| SODIUM HYDROGEN CARBONATE | 5 |

Example B8

| INCI Name | % |
| --- | --- |
| WATER | QS 100 |
| ISOPROPYL PALMITATE | 4 |
| CETYL ALCOHOL | 3.5 |
| STEARYL ALCOHOL | 2.5 |
| CETEARETH 20 | 3 |
| SORBITAN MONOSTEARATE | 2 |
| DIMETHICONE 20 CST | 2 |
| PROPYL PARABEN | 0.1 |
| GLYCEROL | 4 |
| XANTHAN GUM | 0.5 |
| MAGNESIUM ALUMINUM SILICATE | 1 |
| METHYL PARABEN | 0.2 |
| DISODIUM EDTA | 0.05 |
| SODIUM HYDROGEN CARBONATE | 5 |
| OLEYL ALCOHOL | 2 |
| PROPYLENE GLYCOL | 2 |
| PHENOXYETHANOL | 1 |
| SODIUM HYDROXYDE | QS pH |
| IVERMECTIN | 2 |

Example B9

| INCI Name | % |
| --- | --- |
| WATER | QS 100 |
| DISODIUM EDTA | 0.1 |
| XANTHAN GUM | 0.5 |
| ACRYLAMIDE, AMPS COPOLYMER DISPERSION 40%/ISOHEXADECANE/POLYSORBATE 80 | 1.5 |
| CETOSTEARYL ALCOHOL | 3 |
| CETEARETH-20 | 3 |
| GLYCERYL DIBEHENATE | 3 |
| CYCLOPENTASILOXANE | 2 |
| PPG-11 STEARYL ETHER | 5 |
| SODIUM HYDROGEN CARBONATE | 5 |
| OLEYL ALCOHOL | 2 |
| PROPYLENE GLYCOL | 2 |
| PHENOXYETHANOL | 1 |
| SODIUM HYDROXYDE | QS pH |

Example B10

| INCI Name | % |
| --- | --- |
| WATER | QS 100 |
| SODIUM HYDROXYDE | QS pH |

| INCI Name | % |
|---|---|
| XANTHAN GUM | 0.5 |
| MAGNESIUM ALUMINUM SILICATE | 2.5 |
| CETOSTEARYL ALCOHOL | 3 |
| CETEARETH-20 | 3 |
| GLYCERYL DIBEHENATE | 3 |
| CAPRYLIC/CAPRIC TRIGLYCERIDE | 6 |
| SODIUM HYDROGEN CARBONATE | 5 |
| OLEYL ALCOHOL | 2 |
| PROPYLENE GLYCOL | 2 |
| PHENOXYETHANOL | 0.8 |
| IVERMECTIN | 2 |

The mixtures in a 1:1 weight ratio of the intermediate compositions A and B described above are represented in the table below. A cross at the intersection of two formulation intermediates indicates that the mixture was tested and generated a foam having the desired properties.

| Formulation A | Formulation B | | | | | | | | | |
|---|---|---|---|---|---|---|---|---|---|---|
|  | B1 | B2 | B3 | B4 | B5 | B6 | B7 | B8 | B9 | B10 |
| A1 |  |  |  |  |  | X |  | X |  | X |
| A2 | X | X | X | X | X | X | X | X | X | X |
| A3 | X | X | X | X | X | X | X | X | X | X |
| A4 | X | X | X | X | X | X | X | X | X | X |
| A5 |  |  |  |  |  | X |  | X |  | X |
| A6 | X | X | X | X | X | X | X | X | X | X |
| A7 | X | X | X |  | X | X | X | X | X | X |
| A8 | X | X | X | X | X | X | X | X | X | X |
| A9 | X | X | X | X | X | X | X | X | X | X |
| A10 | X | X | X |  |  | X | X | X | X | X |

Example 2A: Foam Density Measurements

From the formulation examples described in example 1, formulation A for the acidic formulation and formulation B for the basic formulation (containing the gas generator; preferably sodium bicarbonate), density measurements are taken on each of the two intermediate formulations A and B (T0) and measurements are then taken on the foam obtained by mixing these two intermediates.

Density of formulation A4=1.052
Density of formulation B4=1.042
Density of foam A4/B4 (50/50)=0.316

Figure 2:
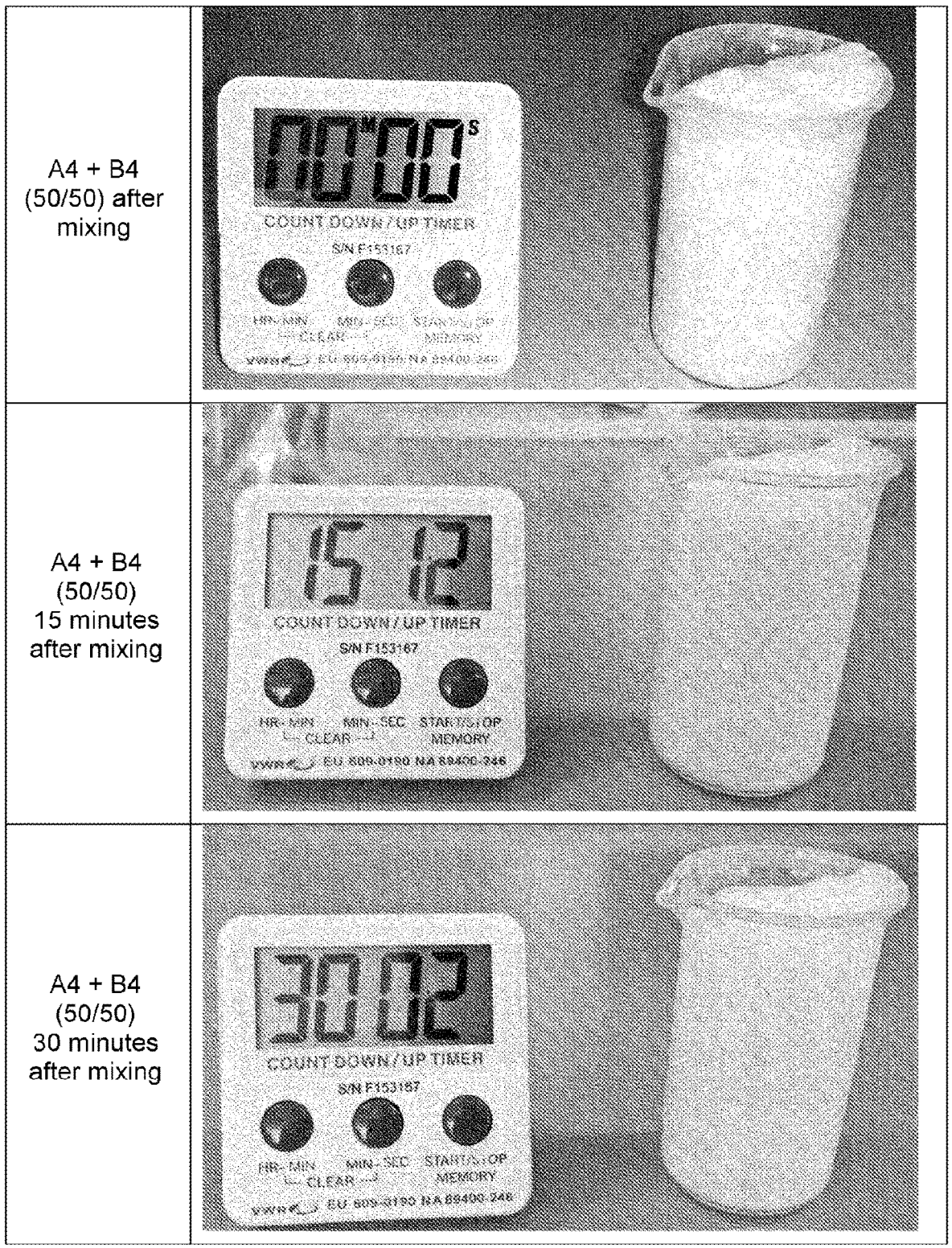
FIG. 2 shows photographs of a foam composition according to the invention and shows that it is stable over time as presented in example 6.

The foam density measurement shows that the volume increased by a factor of 3.3 and was confirmed by the photographs in FIG. 1. The left-hand photo represents the moment of mixing (T0) and the right-hand photo represents the foam obtained when the acid/base chemical reaction is complete.

Example 2B: Stability

Tables Ia, Ib, Ic, Id, Ie and If below collate the physical stability data of the intermediate formulations A2, A4, A6, A8, A9 and A10 described in example 1, containing ivermectin.

TABLE Ia

| Formulation A2 | T0 | | T1 Month | T3 Months | T3 Months |
|---|---|---|---|---|---|
| Macroscopic appearance | Smooth, opaque, thick white emulsion | RT | Complies | Complies | Complies |
|  |  | 40° C. | Complies | Complies | Complies |
| Microscopic observations X400 | Emulsion oil droplets less than 4 μm | RT | Complies | Complies | Complies |
|  |  | 40° C. | Complies | Complies | Complies |
| Brookfield RV DVII Spindle 5, speed 5 Viscosity cP | 570400 | RT | 57840 | 66000 | 65600 |
|  |  | 40° C. | — | — | 77500 |
| pH | 3.42 | RT | 3.54 | 3.61 | 3.61 |
|  |  | 40° C. | 3.73 | 3.92 | 3.84 |

TABLE Ib

| Formulation A4 | T0 | | T1 Month | T3 Months | T3 Months |
|---|---|---|---|---|---|
| Macroscopic appearance | Smooth, opaque, fluid white emulsion | RT | Complies | Complies | Complies |
|  |  | 40° C. | Complies | Complies | Complies |
| Microscopic observations X400 | Emulsion oil droplets less than 10 μm | RT | Complies | Complies | Complies |
|  |  | 40° C. | Complies | Complies | Complies |

TABLE Ib-continued

| Formulation A4 | T0 | | T1 Month | T3 Months | T3 Months |
|---|---|---|---|---|---|
| Brookfield RV DVII Spindle 5, speed 5 Viscosity cP | — | RT | 37120 | 37760 | 37200 |
| | | 40° C. | 40320 | 34650 | 32080 |
| pH | 3.47 | RT | 3.36 | 3.44 | 3.37 |
| | | 40° C. | 3.48 | 3.52 | 3.36 |

TABLE Ic

| Formulation A6 | T0 | | T1 Month | T2 Months | T3 Months |
|---|---|---|---|---|---|
| Macroscopic appearance | Opaque, smooth, slightly thick off-white emulsion | RT | Complies | Complies | Complies |
| | | 40° C. | Complies | Complies | Complies |
| Microscopic observations X400 | Emulsion oil droplets less than 55 μm | RT | Complies | Complies | Complies |
| | | 40° C. | Complies | Complies | Complies |
| Viscosity cP Brookfield LV DVII Spindle 5, speed 10 | 15720 | RT | 13640 | 13480 | 14000 |
| | | 40° C. | 14840 | 13680 | 13640 |
| pH | 3.52 | RT | 3.43 | 3.56 | 3.80 |
| | | 40° C. | 3.56 | 3.69 | 3.79 |

TABLE Id

| Formulation A8 | T0 | | T1 Month | T3 Months |
|---|---|---|---|---|
| Macroscopic appearance | Smooth, opaque, thick white emulsion | RT | Complies | Complies |
| | | 40° C. | Complies | Complies |
| Microscopic observations X400 | Emulsion oil droplets less than 20 μm | RT | Complies | Complies |
| | | 40° C. | Complies | Complies |
| Brookfield RV DVII Spindle 5, speed 5 Viscosity cP | 22000 | RT | 20160 | 23680 |
| | | 40° C. | 23680 | 20800 |
| pH | 3.36 | RT | 3.77 | 3.44 |
| | | 40° C. | 3.57 | 3.41 |

TABLE Ie

| Formulation A9 | T0 | | T1 Month | T3 Months |
|---|---|---|---|---|
| Macroscopic appearance | Smooth, opaque, fluid white emulsion | RT | Complies | Complies |
| | | 40° C. | Complies | Complies |
| Microscopic observations X400 | Emulsion oil droplets less than 20 μm | RT | Complies | Complies |
| | | 40° C. | Complies | Complies |
| Brookfield RV DVII Spindle 5, speed 5 Viscosity cP | 22240 | RT | 18400 | 20720 |
| | | 40° C. | 17760 | 20880 |
| pH | 3.47 | RT | 3.36 | 3.44 |
| | | 40° C. | 3.48 | 3.52 |

TABLE If

| Formulation A10 | T0 | | T1 Month | T3 Months | T3 Months |
|---|---|---|---|---|---|
| Macroscopic appearance | Fluid, opaque, smooth beige gel | RT | Complies | Complies | Complies |
| | | 40° C. | Complies | Complies | Complies |
| Microscopic observations X400 | Homogeneous dispersion less than 100 μm | RT | Complies | Complies | Complies |
| | | 40° C. | Complies | Complies | Complies |

TABLE 1f-continued

| Formulation A10 | T0 | | T1 Month | T3 Months | T3 Months |
|---|---|---|---|---|---|
| Brookfield RV DVII Spindle 4, speed 20 Viscosity cP | 5200 | RT<br>40° C. | 4220<br>4180 | 4140<br>4200 | 4160<br>4140 |
| pH | 3.36 | RT<br>40° C. | 3.86<br>3.74 | 3.86<br>3.92 | 3.89<br>3.97 |

The tables below collate the chemical stability data for ivermectin in these same intermediate formulations, and also in formulations B6 and B10.

| Formulation A2 | T0 | | T1 Month | T2 Months | T3 Months |
|---|---|---|---|---|---|
| % ivermectin (HPLC) | 98.1 | RT<br>40° C. | 97.4<br>— | 98.8<br>92.9 | 99.4<br>95.8 |

| | T0 | | T1 Month | T2 Months | T3 Months |
|---|---|---|---|---|---|
| Formulation A4 | | | | | |
| % ivermectin (HPLC) | 98.0 | RT<br>40° C. | 97.1<br>— | 98.2<br>95.8 | 96.1<br>95.3 |
| Formulation A6 | | | | | |
| % ivermectin (HPLC) | 95.1 | RT<br>40° C. | 95.4<br>95.2 | 95.3<br>94.1 | 93.6<br>91.7 |

| Formulation A8 | T0 | | T1 Month | T2 Months |
|---|---|---|---|---|
| % ivermectin (HPLC) | 96.3 | RT<br>40° C. | 96.2<br>96.1 | 95.2<br>92.9 |

| Formulation A9 | T0 | | T1 Month | T2 Months |
|---|---|---|---|---|
| % ivermectin (HPLC) | 97.2 | RT<br>40° C. | 97.4<br>96.1 | 96.2<br>91.8 |

| Formulation A10 | T0 | | T1 Month | T2 Months |
|---|---|---|---|---|
| % ivermectin (HPLC) | 97.3 | RT<br>40° C. | 96.2<br>96.1 | 96.9<br>97.7 |

| Formulation B6 | T0 | | T1 Month | T2 Months | T3 Months |
|---|---|---|---|---|---|
| % ivermectin (HPLC) | 96 | RT<br>40° C. | 96.9<br>— | 97.6<br>93.5 | 97.6<br>93.4 |

| Formulation B10 | T0 | | T1 Month | T2 Months | T3 Months |
|---|---|---|---|---|---|
| % ivermectin (HPLC) | 97.7 | RT<br>40° C. | 96.7<br>— | 97.5<br>88.5 | 98.3<br>93.6 |

Example 3: Comparative Study of Measurement of Irritation

Study Protocol.

The study is performed according to the OECD TG 439 protocol in force for the short application time (RHE/product contact time 15 min). This protocol is appropriate for a long application time (RHE/product contact time 18 h).

The objective of this study is to evaluate the tolerance of the supports of the complete and intermediate formulations on reconstructed human epidermides (RHE, Episkin model) through:
   evaluation of the reduction of MTT (cell viability)
   measurement of the release of IL-1alpha (irritation marker)

The formulations tested are:
   An intermediate composition of acidic formulation: placebo example A7 (i.e. not containing ivermectin),
   An intermediate composition of basic formulation: example B7,
   The complete formulation composed of the mixture: A7 placebo+B7 (in a 50/50 weight ratio),
   A commercial reference in cream form.

Study Results:

| Mixture tested | Short exposure Viability (%) | Long exposure Viability (%) | Conclusion Irritant potential |
|---|---|---|---|
| B7 | 89.8 | 93.3 | Non-irritant |
| A7 placebo | 86.0 | 84.5 | Non-irritant |
| Complete formulation | 95.8 | 83.4 | Non-irritant |
| Commercial ref. | 99.8 | 91.1 | Non-irritant |

| Test item | Short exposure IL-1a vs control | Long exposure IL-1a vs control |
|---|---|---|
| B7 | 1.5 | 2.0 |
| A7 placebo | 2.2 | 2.3 |
| Complete formulation | 1.9 | 3.1 |
| Commercial ref. | 2.4 | 3.6 |

The MTT measurements according to the OECD protocol in force indicate that all the formulations tested are non-irritant.

The assay of IL-1a of the complete formulation according to the invention after a short exposure time and a long exposure time shows a lower content of irritation markers than after application of the commercial reference.

Example 4

The ideal content of citric acid, sodium pyrophosphate and sodium dihydrogen phosphate monohydrate to react with 5% of sodium bicarbonate was established empirically. The values are expressed as weight/weight percentages relative to the weight of each of the two intermediate formulations.

|  | Ratio 1 | Ratio 2 | Ratio 3 |
|---|---|---|---|
| Sodium bicarbonate | 5% | 5% | 5% |
| Citric acid | 3.5% | — | — |
| Disodium pyrophosphate | — | 12 | — |
| Sodium dihydrogen phosphate monohydrate | — | — | 7.2% |

In order for the pH of the formulation containing the gas activator to have optimum compatibility with the skin, sodium citrate was added so as to create a citric acid/sodium citrate buffer.

Part of the citric acid/sodium citrate buffer may advantageously be replaced with disodium pyrophosphate and vice versa like the contents cited by way of example in table I below:

TABLE III the values are expressed as weight/weight percentages relative to the weight of each of the two intermediate formulations.

|  | E 1 | E 2 | E 3 | E 4 | E 5 | E 6 | E 7 |
|---|---|---|---|---|---|---|---|
| Sodium bicarbonate | 5% | 5% | 5% | 5% | 3% | 3% | 3% |
| Citric acid | 3.5% | 1.75% | 1.4% | 0 | 2.1% | 1.05% | 0 |
| Sodium citrate | 2.7% | 1.3% | 1% | 0 | 1.6% | 1.15% | 0 |
| Disodium pyrophosphate | 0 | 6% | 7.2% | 12% | 0 | 3.6% | 7.2% |

Part of the citric acid/sodium citrate buffer may advantageously be replaced with sodium dihydrogen phosphate monohydrate and vice versa, like the contents cited by way of example in table IV below:

TABLE IV the values are expressed as weight/weight percentages relative to the weight of each of the two intermediate formulations.

|  | E1 | E8 | E9 |
|---|---|---|---|
| Sodium bicarbonate | 5% | 5% | 5% |
| Citric acid | 3.5% | 1.5% | 0 |
| Sodium citrate | 2.7% | 0.5% | 0 |
| Sodium dihydrogen phosphate monohydrate | 0 | 6.2% | 10% |

In one particular embodiment, it was determined that when the amount of citric acid is greater than or equal to 1.4, the amount of foam is optimal when disodium pyrophosphate is present in the composition according to the following equation:

$$[C]=2.4[B]-2.4[A]/0.7$$

when:

$[C]$=weight content of disodium pyrophosphate in the intermediate composition A $[A]$=weight content of citric acid monohydrate in the intermediate composition A $[B]$=weight content of sodium bicarbonate in the intermediate composition B The above equation thus makes it possible to calculate the optimum contents between sodium bicarbonate, citric acid and sodium pyrophosphate.

Example 5: Comparative Study of Release Profile-Permeation

The aim of this study is to evaluate the penetration and distribution of various formulations according to the invention in human skin.

Study Protocol:

The formulations tested in this study are applied to excised whole human skin samples mounted on a Franz cell at a rate of 5 mg/cm$^2$ at 32° C.

After 16 hours of application, ivermectin is assayed in: the fraction not absorbed, the stratum corneum, the epidermis, the dermis and the receiver fluid.

This study makes it possible to study the influence of the formulation on the release of the active principle and its permeation through the skin. The object is to compare the distribution of ivermectin in the various skin layers during the application of a well-known formulation and the application of a composition in chemical foam form.

The formulations tested are:
A reference formulation in cream form containing 1% ivermectin
A complete chemical foam formulation containing 1% ivermectin, composed of the mixture: A4+B9 (in a 50/50 weight ratio),
A complete chemical foam formulation containing 1% ivermectin, composed of the mixture: A5+B10 (in a 50/50 weight ratio), Diffusion Cells:

The diffusion cells used are static diffusion cells, on the basis of the Franz model diffusion cell, with the following characteristics:

Application area=2 cm$^2$

Volume of the receiver fluid compartment=3 ml

The receiver compartment is surrounded by a water jacket heated at 37° C.±1° C. to ensure a temperature of 32° C.±1° C. at the skin surface. The receiver compartment is separated from the donor compartment by the skin membrane, the epidermal face being on the donor side. The receiver compartment containing a magnetic stirring bar was filled with the receiver fluid so as to prevent any formation of air bubbles. During the diffusion time, the receiver fluid was stirred continuously so as to ensure homogenization.

Preparation of the Skin Samples:

Abdominal skin samples derived from cosmetic surgery were used in this study. On arrival of the samples, the hypodermis was separated from the assembly using tweezers, and the remaining material was washed gently and stored flat in aluminum foil for storage at −20° C. On the day of the experiment, the skin samples were thawed and then cut into pieces to be compatible with the geometry of the diffusion cell.

The skin samples, derived from donors 42, 44 and 69 years old, were mounted on the diffusion cell with PBS as receiver fluid. The mean skin thickness was 0.89±0.07 mm with a maximum of 1.39 mm and a minimum of 0.45 mm. Thicknesses of all the specimens.

After at least 45 minutes at equilibrium with the receiver fluid, the skin integrity was evaluated by measuring the trans-epidermal water loss (TEWL). All the cells whose TEWL measurements were outside the acceptance criteria are carefully cleaned and left at equilibrium for a prolonged period before remeasuring the TEWL. The mean TEWL value was 5.51±1.63 g/m²/h.

Figure 3:
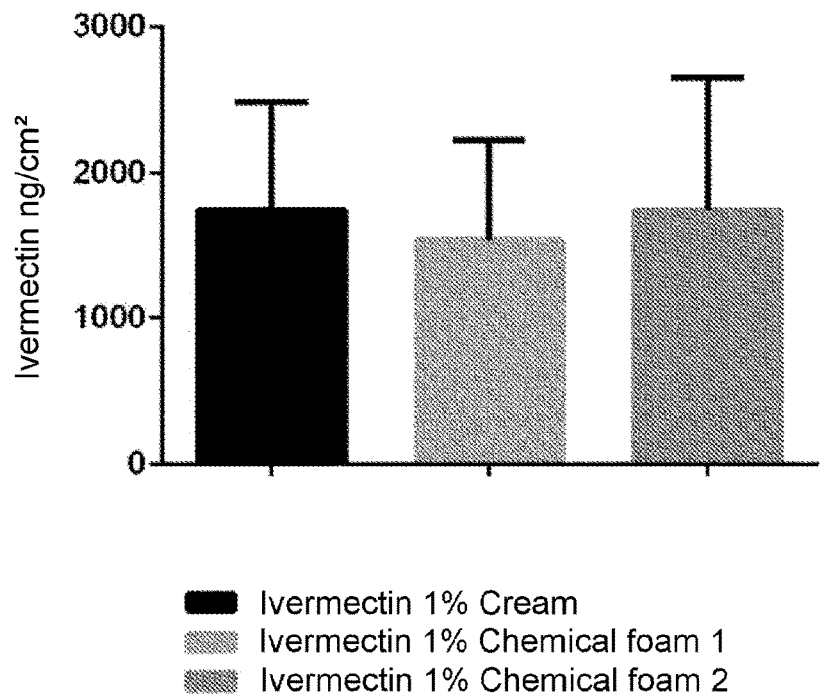
FIGS. 3, 4 and 5 illustrate the results of a comparative study of release profile-permeation in the skin between a composition according to the invention and a reference composition, described in example 5.

Study Parameters:
Room temperature: 21.7° C.
Relative humidity 45.6%
Study Results:

In the stratum corneum, there were no significant differences in cutaneous penetration between the foam formulations according to the invention and the reference, as illustrated in FIG. 3.

Figure 4:
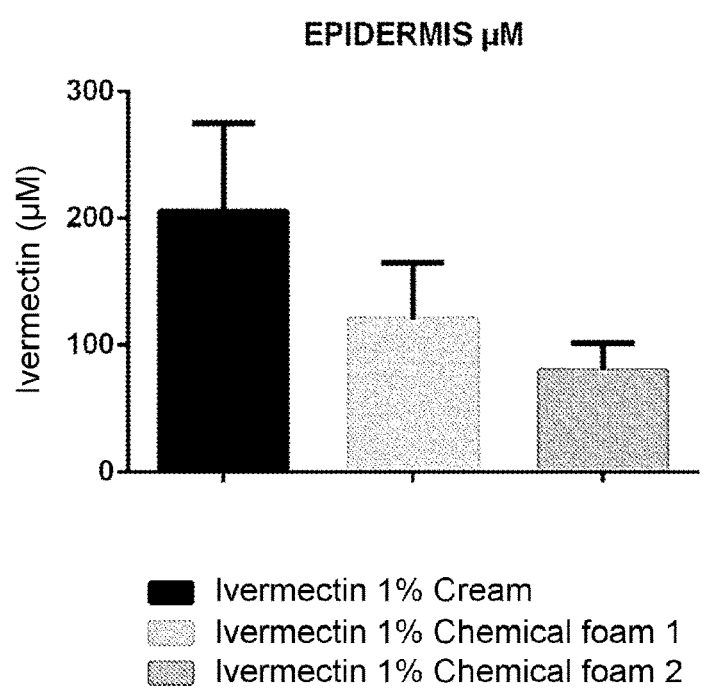

In the epidermis, the chemical foam formulations penetrate less than the reference, in particular for foam 2 (according to example A5+B10 as a 50:50 mixture), as illustrated in FIG. 4.

Figure 5:
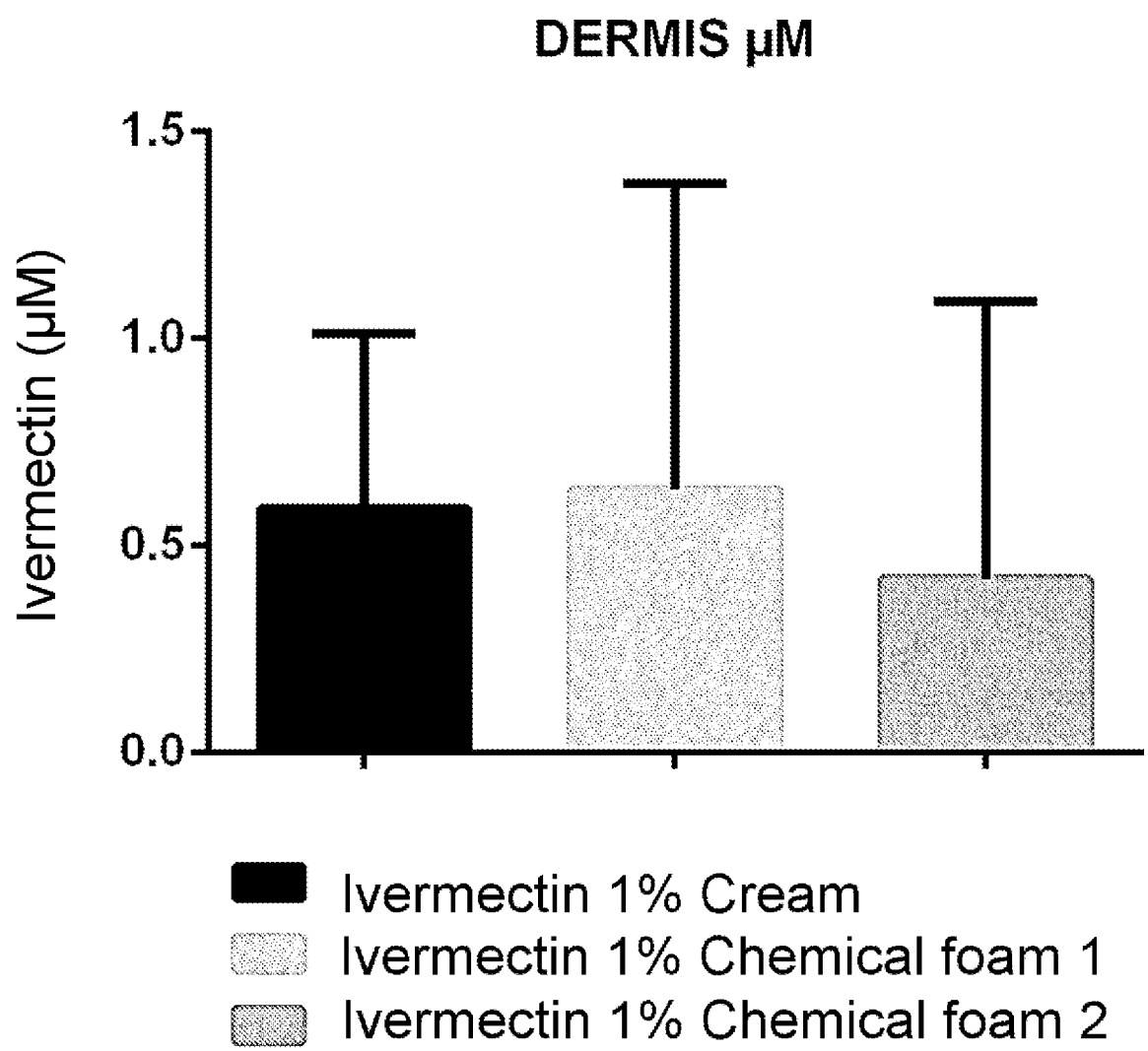

In the dermis, no significant difference was observed (FIG. 5), although a slight difference was observed with the chemical foam 2, for which values below the limits for quantification (BLQ) were recorded, whereas all the dermis samples were quantifiable for the other formulations.

None of the receiver fluid samples was quantifiable, irrespective of the test formulation; this suggests low systemic exposure. The present study confirms the need to obtain a foam which remains on the surface of the skin, so as to act efficiently against *Demodex*.

Example 6: Stability of the Foam (Composed of the Mixture of Intermediate Formulations A and B)

In order to demonstrate the noteworthy stability of the foam, mixing of the formulation intermediates A4 and B4 in a 50/50 ratio is performed in a beaker.

The foam formed is photographed at regular intervals. These photographs shown in FIG. 2 show that, 30 minutes after mixing, the foam has the same volume as at T0. These data confirm the noteworthy stability of the foam according to the invention.

The invention claimed is:

1. A self-foaming composition formulated for leave-on topical application, consisting of:
   (a) at least one intermediate composition B consisting of (i) a gas-generating agent, (ii) 0.15% to 5% by weight, relative to the weight of composition B, of gelling agents, and (iii) at least about 65% by weight, relative to the weight of composition B, of water, and (iv) one or more agents selected from the group consisting of ivermectin, dispersants, solubilizers, stabilizers, preserving agents, fatty substances, thickeners, dyes, fragrances, complexing agents, neutralizers, non-foaming emulsifying agents, fillers, sequestrants, reducing agents, odor maskers, plasticizers, softeners, moisturizers, pigments, clays, mineral fillers, mineral colloids, polymers, proteins, nacreous agents, propellants, waxes, oils, optimally paraffins, fatty acids, solid esters of fatty alcohols or of fatty acids, gums and wetting agents;
   (b) at least one intermediate composition A consisting of (i) an agent for activating the gas-generating agent, (ii) 0.15% to 5% by weight, relative to the weight of composition A, of gelling agents, and (iii) at least about 60% by weight, relative to the weight of composition A, of water, and (iv) one or more agents selected from the group consisting of ivermectin, dispersants, solubilizers, stabilizers, preserving agents, fatty substances, thickeners, dyes, fragrances, complexing agents, neutralizers, non-foaming emulsifying agents, fillers, sequestrants, reducing agents, odor maskers, plasticizers, softeners, moisturizers, pigments, clays, mineral fillers, mineral colloids, polymers, proteins, nacreous agents, propellants, waxes, oils, optimally paraffins, fatty acids, solid esters of fatty alcohols or of fatty acids, gums and wetting agents wherein the ivermectin is present in composition A and/or composition B;
wherein the gelling agents do not comprise cellulose or cellulose derivatives; and
wherein at least 90% of the ivermectin remains present in the composition after 2 months at room temperature or 40° C.

2. The composition as claimed in claim 1, wherein the ivermectin is present in the intermediate composition A.

3. The composition as claimed in claim 1, wherein the composition does not comprise any anionic surfactants, cationic surfactants, amphoteric surfactants, and nonionic surfactants of the family of alkylpolyglucosides and glucamides.

4. The composition as claimed in claim 1, wherein the gas generated from the gas-generating agent is carbon dioxide.

5. The composition as claimed in claim 1, wherein the gas-generating agent is selected from the group consisting of sodium bicarbonate, potassium bicarbonate, sodium carbonate and potassium carbonate, and mixtures thereof.

6. The composition as claimed in claim 1, wherein the gas-generating agent is present in the intermediate composition B in an amount ranging from 1% to 10% by weight, relative to the weight of the intermediate composition B.

7. The composition as claimed in claim 1, wherein the intermediate composition B has a pH of from 7 to 12.

8. The composition as claimed in claim 1, wherein the agent for activating the gas-generating agent is selected from the group consisting of an acid, a partially salified polyacid salt, a buffer solution of a weak acid and of its conjugate base, and mixtures of these compounds.

9. The composition as claimed in claim 1, wherein the agent for activating the gas-generating agent is selected from the group consisting of citric acid, tartaric acid, malic acid, lactic acid, phosphoric acid and pyrophosphoric acid, and the salts of these acids.

10. The composition as claimed in claim 1, wherein the agent for activating the gas-generating agent is a citric acid/sodium citrate buffer, alone or as a mixture with sodium phosphate and/or disodium pyrophosphate.

11. The composition as claimed in claim 1, wherein the agent for activating the gas-generating agent is present in the intermediate composition A in an amount ranging from 0.001% to 95% by weight relative to the weight of the intermediate composition A.

12. The composition as claimed in claim 1, wherein the intermediate composition A has an acidic pH.

13. The composition as claimed in claim 1, wherein the intermediate composition A is in the form of a solution, a gel or an emulsion.

14. The composition as claimed in claim 1, wherein the intermediate composition B is in the form of a solution, a gel or an emulsion.

15. A composition in foam form, wherein the composition results from mixing of the intermediate compositions A and B, as claimed in claim 1.

16. A cosmetic method comprising topically applying an effective amount of the composition according to claim 1 to the skin of an individual subject in need thereof.

17. A kit or single multi-compartment container consisting of:
- (a) an intermediate composition B consisting of (i) a gas-generating agent, (ii) 0.15% to 5% by weight, relative to the weight of composition B, of gelling agents, and (iii) at least about 65% by weight, relative to the weight of composition B, of water, and (iv) one or more agents selected from the group consisting of ivermectin, dispersants, solubilizers, stabilizers, preserving agents, fatty substances, thickeners, dyes, fragrances, complexing agents, neutralizers, non-foaming emulsifying agents, fillers, sequestrants, reducing agents, odor maskers, plasticizers, softeners, moisturizers, pigments, clays, mineral fillers, mineral colloids, polymers, proteins, nacreous agents, propellants, waxes, oils, optimally paraffins, fatty acids, solid esters of fatty alcohols or of fatty acids, gums and wetting agents;
- (b) an intermediate composition A consisting of (i) an agent for activating the gas-generating agent, (ii) 0.15% to 5% by weight, relative to the weight of composition A, of gelling agents, and (iii) at least about 60% by weight, relative to the weight of composition A, of water, and (iv) one or more agents selected from the group consisting of ivermectin, dispersants, solubilizers, stabilizers, preserving agents, fatty substances, thickeners, dyes, fragrances, complexing agents, neutralizers, non-foaming emulsifying agents, fillers, sequestrants, reducing agents, odor maskers, plasticizers, softeners, moisturizers, pigments, clays, mineral fillers, mineral colloids, polymers, proteins, nacreous agents, propellants, waxes, oils, optimally paraffins, fatty acids, solid esters of fatty alcohols or of fatty acids, gums and wetting agents;

wherein the ivermectin is present in composition A and/or composition B;

wherein the gelling agents do not comprise cellulose or cellulose derivatives; and wherein at least 90% of the ivermectin remains present in the composition after 2 months at room temperature or 40° C.

18. The kit or container as claimed in claim 17, wherein the kit or container is designed for mixing the intermediate compositions A and B in an AB weight ratio ranging from 0.5 to 2.

19. The composition as claimed in claim 5, wherein the gas-generating agent is sodium bicarbonate.

20. The composition as claimed in claim 6, wherein the gas-generating agent is present in an amount ranging from 2% to 8% by weight.

21. The composition as claimed in claim 7, wherein the pH is basic.

22. The composition as claimed in claim 9, wherein the agent for activating the gas-generating agent is selected from the group consisting of:
- a tartaric acid/tartrate salt buffer;
- a citric acid/sodium citrate buffer alone; and
- phosphoric acid, sodium phosphate, disodium pyrophosphate, which are alone or as a mixture with a citric acid/sodium citrate buffer.

23. The composition as claimed in claim 12, wherein the acidic pH is from 1.0 to 6.0.

24. The kit or container as claimed in claim 18, wherein the A/B weight ratio ranges from 0.5 to 1.5.

25. The kit or container as claimed in claim 18, wherein the A/B weight ratio ranges from 0.9 to 1.1.

26. The kit or container as claimed in claim 18, wherein the A/B weight ratio is 1.

27. The composition as claimed in claim 1, wherein:
- the gelling agents in intermediate composition B are selected from the group consisting of: acrylic acid polymers; polysaccharides selected from xanthan gum, gellan gum, *sclerotium* gum, guar gum and derivatives thereof; magnesium aluminum silicates; modified starches; carrageenans; and combinations thereof; and
- the gelling agents of intermediate composition A are selected from the group consisting of: acrylic acid polymers; polysaccharides selected from xanthan gum, gellan gum, *sclerotium* gum, guar gum and derivatives thereof; magnesium aluminum silicates; modified starches; carrageenans; and polyvinyl alcohols.

28. The kit or container as claimed in claim 17, wherein:
- the gelling agents in intermediate composition B are selected from the group consisting of: acrylic acid polymers; polysaccharides selected from xanthan gum, gellan gum, *sclerotium* gum, guar gum and derivatives thereof; magnesium aluminum silicates; modified starches; carrageenans; and combinations thereof; and
- the gelling agents of intermediate composition A are selected from the group consisting of: acrylic acid polymers; polysaccharides selected from xanthan gum, gellan gum, *sclerotium* gum, guar gum and derivatives thereof; magnesium aluminum silicates; modified starches; carrageenans; and polyvinyl alcohols.

* * * * *